US007892782B2

(12) United States Patent
Coates et al.

(10) Patent No.: US 7,892,782 B2
(45) Date of Patent: Feb. 22, 2011

(54) SCREENING PROCESS FOR ANTIBACTERIAL AGENTS

(75) Inventors: Anthony Robert Milnes Coates, London (GB); Yanmin Hu, London (GB)

(73) Assignee: Helperby Therapeutics Limited, London (GB)

( * ) Notice: Subject to any disclaimer, the term of this patent is extended or adjusted under 35 U.S.C. 154(b) by 125 days.

(21) Appl. No.: 12/343,176

(22) Filed: Dec. 23, 2008

(65) Prior Publication Data

US 2009/0104651 A1    Apr. 23, 2009

Related U.S. Application Data

(63) Continuation of application No. 10/919,354, filed on Aug. 17, 2004, now abandoned, which is a continuation of application No. 09/842,637, filed on Apr. 27, 2001, now abandoned, which is a continuation of application No. PCT/GB99/03728, filed on Nov. 9, 1999.

(60) Provisional application No. 60/107,655, filed on Nov. 9, 1998.

(51) Int. Cl.
    *C12Q 1/18*    (2006.01)
(52) U.S. Cl. ........................................................ 435/32
(58) Field of Classification Search .................... 435/32
    See application file for complete search history.

(56) References Cited

U.S. PATENT DOCUMENTS

| 3,697,648 | A | 10/1972 | Shomura et al. |
| 3,963,576 | A | 6/1976 | Horsfall, III et al. |
| 4,234,579 | A | 11/1980 | Barth |
| 5,684,144 | A | 11/1997 | Romeo |
| 5,686,283 | A | 11/1997 | Gaffney et al. |
| 5,700,925 | A | 12/1997 | Bishai et al. |
| 5,733,774 | A | 3/1998 | Jin et al. |
| 7,094,397 | B2 * | 8/2006 | Stratton et al. ............. 424/85.4 |

FOREIGN PATENT DOCUMENTS

WO    95/34574 A1    12/1995

OTHER PUBLICATIONS

Archer G. Antimicrobial Susceptibility and Selection Resistance . . . Antibacterial Agents and Chemotherapy 14(3)353-359, Sep. 1978.*
Hu Y. et al. Sterilizing Activities of Fluoroquinolones . . . Antbacterial Agents and Chemotherapy 47(2)653-657, Feb. 2003.*
Zak O. et al. Remarks on the Screening of Antibiotics for Antibacterial Activity. European J Clinical Microbiology Infectious Disease 9(7)462-465, Jul. 1990.*
Coates A. et al. Novel Approaches to Developing New Antibiotics for Bacterial Infections. British J Pharmacology 152, 1147-1154, 2007.*
F.J. Boswell et al., "Time-kill kinetics of quinupristin/dalfopristin on *Staphylococcus aureus* with and without a raised MBC evaluated by two methods", Journal of Antimicrobial Chemotherapy, 1997, 39(Suppl. A): 29-32.
José M. Entenza et al., "Antibiotic Treatment of Experimental Endocarditis Due to Methicillin-Resistant *Staphylococcus epidermidis*", The Journal of Infectious Diseases, 1994, 170: 100-109.
José M. Entenza et al., "Importance of Genotypic and Phenotypic Tolerance in the Treatment of Experimental Endocarditis Due to *Streptococcus gordonii*", The Journal of Infectious Diseases, 1997, 175: 70-76.
Elaine Tuomanen et al., "Mechanism of Phenotypic Tolerance of Nongrowing Pneumococci to Beta-lactam Antibiotics", Scand. Journal of Infectious Diseases, Suppl., 1991, 74: 102-112.
MG Bergeron et al., "Tolerance of Haemophilus influenzae to beta-lactam antibiotics", Antimicrob Agents Chemother, 1985, 28(2): 320-325.
GJ Van Asselt et al., "Detection of penicillin tolerance in *Streptococcus pyogenes*", J. Med. Microbiol, 1993, 38(3): 197-202.
Patrick R. Murray et al., Manual of Clinical Microbiology, ASM Press, 1996, pp. 427-428.
Daniel F. Sahm et al., "In Vitro Susceptibility Studies of Vancomycin-Resistant *Enterococcus faecalis*", Antimicrobial Agents and Chemotherapy, 1989, 33(9): 1588-1591.
Michael J. Pelczar, Jr. et al., Laboratory Exercises in Microbiology, 1977, pp. 373-374.
The Merck Index, Merck & Co., Inc., 1996, Item 8382.
Anthony M. George et al., "Amplifiable Resistance to Tetracycline, Chloramphenicol, and Other Antibiotics in *Escherichia coli*: Involvement of a Non-Plasmid-Determined Efflux of Tetracycline", Journal of Bacteriology, 1983, 155(2): 531-540.
Gordon L. Archer, "Antimicrobial Susceptibility and Selection of Resistance Among *Staphylococcus epidermidis* Isolates Recovered from Patients with Infections of Indwelling Foreign Devices", Antimicrobial Agents and Chemotherapy, 1978, 14(3): 353-359.
Hervé Lelièvre et al., "Emergence and Spread in French Hospitals of Methicillin-Resistant *Staphylococcus aureus* with Increasing Susceptibility to Gentamicin and Other Antibiotics", Journal of Clinical Microbiology, 1999, 37(11): 3452-3457.
Linda K. Dillon et al., "Early Detection of Oxacillin-Resistant Staphylococcal Strains with Hypertonic Broth Diluent for Microdilution Panels", Journal of Clinical Microbiology, 1984, 19(4): 473-476.
Harry Eagle et al., "The Slow Recovery of Bacteria From the Toxic Effects of Penicillin", J. Bacteriol., 1949, 58(4): 475-490.
Gary K. Best et al., "Evidence for Participation of Autolysins in Batericidal Action of Oxacillin on *Staphylococcus aureus*", Antimicrobial Agents and Chemotherapy, 1974, 6(6): 825-830.
Reinhold, "Paramedical Microbiology", 1963, New York XP002130014, pp. 230-243.

* cited by examiner

*Primary Examiner*—Ralph Gitomer
(74) *Attorney, Agent, or Firm*—Marshall, Gerstein & Borun LLP (57) ABSTRACT

The present invention relates to a method of preparing a phenotypically antibiotic-resistant subpopulation of stationary phase bacteria by treating stationary phase bacteria with high doses of antibacterial agents, the subpopulation thus identified, a process for identifying new antibacterial agents by testing against the antibiotic-resistant subpopulation, the compounds thus identified and their uses, particularly in treating bacterial infections involving dormant bacteria.

15 Claims, 3 Drawing Sheets

SCREENING PROCESS FOR ANTIBACTERIAL AGENTS

This application is a Continuation of U.S. application Ser. No. 10/919,354, filed Aug. 17, 2004 now abandoned, which is a Continuation of U.S. application Ser. No. 09/842,637 filed Apr. 27, 2001, now abandoned, which is a Continuation of PCT/GB99/03728 (published under PCT Article 21(2) in English) filed Nov. 9, 1999 (which claims benefit of priority under 35 U.S.C. §365(c) and §120), which claims benefit under 35 U.S.C. §119(e) of U.S. Provisional Application No. 60/107,655 filed Nov. 9, 1998. The entire disclosures of the prior applications, application Ser. Nos. 10/919,354, 09/842, 637, PCT/GB99/03728 and 60/107,655 are considered part of the disclosure of the accompanying continuation application, and are hereby incorporated by reference.

The present invention relates to the isolation of subpopulations of stationary phase bacteria which exhibit resistance to conventional antibacterial agents, to the use of such resistant subpopulations in screening processes for the identification of new and improved antibacterial agents, to novel antibacterial agents identified thereby, and to therapeutic applications of such antibacterials.

Tuberculosis remains a serious disease throughout the world and it has been estimated that deaths resulting from tuberculosis account for 7% of the total number of deaths from infectious diseases. As discussed in U.S. Pat. No. 5,700, 925, the vast majority of individuals who become infected with *Mycobacterium tuberculosis* do not develop symptomatic tuberculosis but do exhibit a positive reaction to the tuberculin skin test. In such infected hosts, some bacteria persist in a dormant or latent state in which they are substantially resistant to antimicrobial drugs. Over a lifetime, up to 10% of these infected but asymptomatic individuals may go on to develop tuberculosis, often many years after primary infection, when the dormant bacilli become activated and start to grow. This can result in pulmonary tuberculosis and other variant forms of the disease. Factors which predispose towards activation of the dormant organism and manifestation of the diseased state include poverty, poor living conditions, malnutrition, immune deficiency or immune suppression.

In general in the treatment of tuberculosis, antimicrobial therapy using antibacterial agents such as rifampicin, isoniazid and/or pyrazinamide is relatively successful against actively growing bacteria. Such therapy is ineffective, however, against bacteria which remain dormant or which, having undergone a growing phase, re-enter a dormant phase. This causes particular problems in the clinical treatment of tuberculosis sufferers and carriers because the resistance of the dormant organisms necessitates long term chemotherapeutic care. Such long term treatment, typically of six months duration, is unsatisfactory since it is expensive, may result in poor patient compliance and may encourage the development and emergence of antibiotic resistant strains of bacteria over and above the *M. tuberculosis* targeted during therapy.

It is believed that most pathogenic bacteria for example *Staphylococcus aureus, Haemophilus influenzae, Streptococcus pyogenes, Streptococcus gordonii* and *E. coli*, possess a similar substantially antibacterial agent-resistant subpopulation which may act as a pool for reinfection during or after chemotherapy. These persistent bacteria are usually drug-sensitive at relapse, indicating that their resistance to chemotherapy is phenotypic rather than genetic.

In order to investigate whether the metabolism of such persistent bacteria is switched off with no cell division (i.e. is spore-like) or is active (i.e. so that the cells will contain markers of metabolism such as mRNA), we have studied *M. tuberculosis* in an in vitro stationary phase model obtained by long term culturing of the organisms in a microaerophilic gradient in which the stationary phase organisms are viable. Such stationary phase bacteria were found to be resistant to rifampicin at the normal minimum inhibitory concentration (MIC) level of 0.1 µg/ml (as assessed with bacteria at concentration of $10^6$-$10^7$ cfu/ml). Viability of *M. tuberculosis* in vivo before and after treatment with anti-tuberculosis agents has also been examined. Viable persistent non-culturable bacteria were present after treatment with antibacterials, whose dormancy was reversed when the host animals were subjected to steroid therapy.

The present invention is based on the unexpected and surprising finding that, whilst treatment of such stationary phase bacteria with antibacterial agents such as rifampicin at concentrations greatly exceeding the minimum inhibitory concentration reduces plate counts to zero colony forming units (CFU's), there remains a small number of persistent organisms which are detectable by, for example, broth dilution counting. These resistant subpopulations are phenotypically resistant to rifampicin, since they become sensitive to rifampicin at normal MIC levels upon resumption of growth.

Analogous studies using stationary phase *E. coli* and *S. aureus* model systems and treatment thereof with kanamycin and ampicillin respectively have yielded similar results.

In a first aspect, the present invention thus provides a method of preparing a phenotypically antibiotic-resistant subpopulation of stationary phase bacteria comprising at least the steps of:

(i) growing a bacterial culture to stationary phase; and (ii) treating said stationary phase culture with one or more antibacterial agents at a concentration and for a time sufficient to kill growing bacteria, thereby selecting a phenotypically antibiotic-resistant subpopulation.

As referred to herein, the "phenotypically antibiotic-resistant" bacteria refers to a portion of the stationary phase bacteria which remain metabolically active (e.g. as examined by transcriptional activity) after treatment of the stationary phase bacteria with a particular antibiotic (or more than one antibiotic) administered at a high dosage, namely at least 10 times higher than MIC. This subpopulation is however susceptible to treatment with the antibiotic when not in the stationary phase. It will be appreciated that a subpopulation of bacteria resistant to a particular antibiotic may be distinct to a subpopulation resistant to a different antibiotic.

As referred to herein "kill" refers to a loss of viability as assessed by a lack of metabolic activity. In order to achieve this effect, antibiotic is administered to the stationary phase for an appropriate time and at an appropriate concentration. Conveniently antibiotic is applied at a concentration of from 10 to $10^4$×MIC, e.g. at a concentration of 25 to 150 µg/ml (e.g. 50 to 100 µg/ml) with the bacteria at a concentration of $10^5$ to $10^9$ bacteria/ml (e.g. $10^6$ to $10^7$ bacterial/ml). Conveniently bacteria are treated with the anti-bacterial agent(s) for 1-10 days, e.g. 3-5 days.

The nature of the antibacterial agent employed may depend on the particular bacteria being investigated. The use of antibacterial agents such as rifampicin which target RNA polymerase, for example at concentrations of $10^2$, $10^3$ or $10^4$ times the normal MIC level, has been found convenient. In a representative embodiment of this aspect of the invention, treatment of stationary phase *M. tuberculosis* at a level of $10^6$ bacteria/ml for one day with 100 µg/ml of rifampicin (MIC× $10^3$) resulted in a phenotypically resistant subpopulation of $10^2$ bacteria/ml. Alternatively, *M. tuberculosis* may be treated with pyrazinamide. In further embodiments, treatment of stationary phase *B. coli* or *S. aureus* ($\cong 10^9$ bacteria/ml) with 50 µg/ml kanamycin or 100 µg/ml ampicillin for 3 days results in a phenotypically resistant subpopulation of $\cong 10^5$ bacteria/ml.

The phenotypically antibiotic-resistant subpopulation may be seen as representative of the persistent bacteria which remain metabolically active in vivo and which can result in relapse or onset of disease. Of interest therefore in particular are antibiotic-resistant populations from bacteria which exhibit dormancy in vivo, e.g. bacteria from the genera *Staphylococcus*, *Escherichia*, *Hemophilus* and *Mycobacterium*. Particularly preferred are subpopulations from the bacteria *Staphylococcus aureus*, *Escherichia coli*, *Haemophilus influenzae*, *Streptococcus pyogenes*, *Streptococcus gordonii* and *Mycobacterium tuberculosis*.

In particularly preferred features, the bacteria are *Mycobacterium tuberculosis*, *Escherichia coli* and *Staphylococcus aureus* treated with rifampicin, kanamycin and ampicillin, respectively.

Such phenotypically resistant subpopulations of stationary phase bacteria, obtainable by treating stationary phase bacteria with a high dosage of an antibacterial agent, constitute a further feature of the present invention.

On the basis that the phenotypically resistant subpopulations of the invention mimic the behaviour of dormant bacteria in vivo, they constitute valuable tools in screening procedures designed to identify potentially valuable new antibacterial agents. It will be appreciated that antibacterial agents having activity against such phenotypically resistant subpopulations may have great therapeutic potential in the treatment of diseases such as tuberculosis in which dormant bacteria provide a pool for reinfection.

Thus, in a further aspect, the present invention provides a process for assessing the antibacterial activity of a test compound or agent or for identifying or isolating a compound or agent having antibacterial activity against stationary phase bacteria comprising the steps of:

(i) growing a bacterial culture to stationary phase;

(ii) treating said stationary phase culture with one or more antibacterial agents at a concentration and for a time sufficient to kill growing bacteria, thereby selecting a phenotypically resistant subpopulation;

(iii) incubating a sample of said phenotypically resistant subpopulation with one or more test compounds or agents; and (iv) assessing any antibacterial effects against said phenotypically resistant subpopulation and optionally isolating a compound or agent exhibiting antibacterial activity.

Such a process facilitates the rapid screening of large numbers of compounds quickly and efficiently. The compounds to be screened may be any chemical compounds and may be already known or may themselves be novel. Especially suitable candidate compounds are the products of combinatorial chemistry, phage display libraries, natural products, synthetic, semi-synthetic or natural homologues, analogues, derivatives and precursors of known antimicrobial agents or other pharmaceuticals. Such homologues, analogues, derivatives and precursors are entities which are related to or derived from naturally occurring antimicrobials or other pharmaceuticals, e.g. where this is a protein or peptide by single or multiple amino acid substitution, addition and/or deletion or alteration of the level of glycosylation, or if the antimicrobial is a chemical compound by chemical derivatization, e.g. esterification, addition of various substituents, methylation etc. Preferably the above described modifications will not affect the principal function of the molecule, e.g. they will retain antimicrobial activity although the extent of this activity may be modified.

To perform the test, conveniently 1-1000 µl, e.g. 50-300 µl of the prepared antibiotic-resistant bacteria (which is washed prior to use) containing $10^3$ to $10^6$ bacteria/ml are added to the sample to be tested e.g 0.1 to 100 µg, preferably 1-20 µg. These are incubated together at a temperature suitable for metabolic activity, preferably 37° C. Antibacterial effects are then assessed at one or more time points varying from 1 day to 4 weeks, preferably once weekly for 4 weeks.

The term "assessing" as used herein in reference to antibacterial effects includes both quantitation in the sense of obtaining an absolute value of the extent of anti-bacterial activity, and also obtaining a semi-quantitative assessment or other indication, e.g. an index or ratio, of the amount of anti-bacterial activity in the sample. Assessing includes the identification of both positive effects on bacterial activity. The identification and optional isolation of agents or compounds which exhibit anti-bacterial effects is however preferred. Such anti-bacterial effects may be bacteriocidal or bacteriostatic in nature, although the former is preferred.

The existence of anti-bacterial activity may be ascertained by comparing the level of metabolically active or live bacteria in the test sample to control samples. This assessment may be achieved by any appropriate technique which identifies metabolic activity. Thus for example, transcriptional or translational activity may be assessed in respect of one or more genes, e.g. by monitoring gene transcript levels, or more generally, e.g. by monitoring the incorporation of particular bases or amino acids. Alternatively other techniques may be used, e.g. the ability to form colonies may be assessed, e.g. cfu counts may be determined after resuscitation in liquid culture even though direct plating on solid media without intermediate liquid medium culture may fail to yield cfu. Compounds of interest may optionally be re-screened at different concentrations, for example to establish the MIC level.

Compounds or agents having anti-bacterial activity are considered to be those which, at the concentration used, adversely affect the metabolic activity of the phenotypically antibiotic-resistant subpopulation, preferably by reducing metabolic activity to less than 50%, especially preferably less than 25%, e.g. less than 10% compared to untreated control samples.

Candidate compounds identified in such a manner, for example exhibiting a minimum inhibitory concentration of 10 µg/ml or less, preferably 1 µg/ml or less, especially preferably 0.1 µg/ml (as assessed with bacteria at a concentration of $10^6$ to $10^7$ cfu/ml) in respect of the resistant subpopulation, may then be subjected to further analysis, efficacy and toxicity tests etc.

The invention furthermore extends to kits for performing the screening method of the invention. Thus the present invention provides a kit for assessing the antibacterial activity of a test compound or identifying an antibacterial agent, comprising at least the following:

i) a phenotypically antibiotic-resistant subpopulation of stationary phase bacteria as defined herein.

Preferably the kit also contains appropriate buffers and solutions (particularly for maintaining the bacteria, e.g. including appropriate antibacterial agents) for assessing antibacterial effects of the test compound or agent by ascertaining metabolic activity of the bacteria. Additionally, the kit may also include means for standardization of the assay or for comparative purposes.

Compounds or antibacterial agents identified or isolated by the above mentioned process are preferably produced on a larger scale for further testing or use. Depending on the nature of the test compounds this may be achieved using synthetic or natural processes or a combination of both. For example, where the test compound is a peptide this may be produced synthetically by peptide synthesis or may be produced by expression of an appropriate DNA molecule. Thus in a preferred aspect, the present invention provides a process for preparing an agent having anti-bacterial activity against stationary phase bacteria wherein said agent identified according to the process described herein is amplified.

In a further aspect, the present invention is directed towards novel chemical compounds which exhibit bacteriostatic or bactericidal effects on an antibacterial agent resistant subpopulation of stationary phase bacteria, e.g. a rifampicin-resistant subpopulation of *M. tuberculosis*, a kanamycin-resistant is subpopulation of *E. coli* or an ampicillin-resistant subpopulation of *S. aureus*. In particular, the present invention provides antibacterial agents identified by the above described process.

It is believed that resistance of persistent bacteria to antibacterial agents may be due to a decrease in cell wall permeability and/or the use of alternative sigma factors (such as sigB). New antibacterial agents which have the effect of increasing cell wall permeability or inhibiting the use of alternative sigma factors are therefore especially preferred.

Anti-bacterial agents identified according to the invention have particular utility in the treatment of diseases or disorders in which dormant bacteria provide a pool from which symptomatic disease may be initiated or restarted. In particular diseases resulting from pathogenic bacteria of the genera *Staphylococcus, Escherichia, Hemophilus* and *Mycobacterium* may be targeted. Anti-bacterial agents having activity against the persistent bacteria may be used during symptomatic or asymptomatic stages of the disease or condition, when those persistent bacteria are dormant or in a non-dormant state, and optionally may be used in conjunction with agents directed to non-dormant bacteria. "Non-dormant bacteria" as used herein includes bacteria which at the time are in a non-dormant state, ie. are actively growing, but may or may not at other times exhibit a dormant state.

In another aspect therefore, the present invention is directed towards a composition or formulation comprising a novel antimicrobial e.g. antibacterial agent or chemical compound as described herein and a pharmaceutically acceptable diluent or excipient.

By "pharmaceutically acceptable" is meant that the ingredient must be compatible with other ingredients of the compositions as well as physiologically acceptable to the recipient.

Pharmaceutical compositions according to the invention may be formulated in conventional manner using readily available ingredients. Thus, the active ingredient may be incorporated, optionally together with other active substances, with one or more conventional carriers, diluents and/or excipients, to produce conventional galenic preparations such as tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, sterile packaged powders, and the like.

Example of suitable carriers, excipients, and diluents are lactose, dextrose, sucrose, sorbitol, mannitol, starches, gum acacia, calcium phosphate, aglinates, tragacanth, gelatin, calcium silicate, microcrystalline cellulose, polyvinylpyrrolidone, cellulose, water syrup, water, water/ethanol, water/glycol, water/polyethylene glycol, propylene glycol, methyl cellulose, methylhydroxybenzoates, propyl hydroxybenzoates, talc, magnesium stearate, mineral oil or fatty substances such as hard fat or suitable mixture thereof.

In the clinical management of tuberculosis and other disease states where the establishment and existence of dormant bacteria is problematic, it may be advantageous to administer a combination of antibacterial agents which are respectively directed towards the different growth phases of these organisms. Thus, for example, an appropriate chemotherapeutic approach to the treatment of tuberculosis and similar diseases would be to administer to a patient one or more antibacterial agents directed against the growing or log-phase of the microorganisms and one or more antibacterial agents directed against the dormant or stationary phase population.

Thus, a preferred formulation according to the present invention comprises at least one antibacterial agent which has activity against actively growing bacteria and at least one antibacterial agent or chemical compound (as described herein) having activity against the phenotypically resistant subpopulation of the stationary phase of said bacteria. Such formulations may be presented as a combined preparation for simultaneous, separate or sequential use in the treatment of bacterial infections such as tuberculosis.

Such formulations may be administered during symptomatic or asymptomatic stages of the disease, ie. the antibacterial agent against the resistant sub-population need not necessarily be used when these bacteria are in the dormant phase but may be used when they are actively growing.

As used herein antibacterial agents which have activity against actively growing bacteria exhibit antibacterial effects as described hereinbefore against bacteria during the log-phase.

In a further aspect, the present invention provides the compounds or agents, identified as effective against phenotypically resistant subpopulations of stationary phase bacteria, e.g. by the above described screening process, or compositions containing them for use in the treatment of bacterial infection. Conveniently, bacterial infections which may appropriately be treated are those in which persistent bacteria would remain after infection even when the infected macroorganism is asymptomatic, e.g. before the onset of disease or after treatment with known antibacterials. These bacteria may be in the dormant phase and thus in a preferred aspect the bacterial infection to be treated involves (or could potentially involve) dormant bacteria, insofar as the infection is typified or characterized by a subpopulation of persistent bacteria which remain in asymptomatic patients in the absence of actively growing bacteria, ie. which may enter a dormant phase after infection.

In yet another aspect, the present invention relates to the use of compounds or agents identified as effective against phenotypically resistant subpopulations of stationary phase bacteria, e.g. by the above screening process, or compositions containing them in the preparation of a medicament for the treatment of bacterial infections.

The use of such antibacterial compounds identified by the above process in the treatment of bacterial infections (preferably those involving dormant bacteria) constitutes another aspect the present invention.

Alternatively viewed, the present invention provides a method of treatment of a bacterial infection comprising administering to a patient in need of such therapy an effective amount of an antibacterial agent or compound directed towards the stationary phase of growth, optionally in the presence of one or more antibacterial agent directed towards the growing phase of said organism.

In therapeutic methods according to the invention, preferably, the animal to be treated is a mammal, especially preferably a human.

As mentioned above, administration may be made when the diseased individual is symptomatic or asymptomatic. Although the antibacterial agents of the invention may be identified as effective against dormant, persistent, bacteria, ie. in the stationary phase of growth, the agents of the invention may be administered when these bacteria are actively growing.

Administration of the composition may take place by any of the conventional routes, e.g. orally, rectally or parenterally such as by intramuscular, subcutaneous, intraperitoneal or intravenous injection.

The active ingredient in such compositions may comprise from about 0.01% to about 99% weight of the formulation, preferably from about 0.1 to about 50%, for example 10%. The precise dosage of the active ingredient to be administered and the length of the course of treatment will, of course, depend on a number of factors including for example, the age and weight of the patient, the specific condition requiring treatment and its severity, and the route of administration.

In each aspect of the invention, the stationary phase bacteria which are the target of the antibacterial agents may include pathogenic bacteria such as Staphylococcus aureus, Haemophilus influenzae, Streptococcus pyogenes, Streptococcus gordonii, Escherichia coli and particularly preferably, Mycobacterium tuberculosis.

The following non-limitative Examples serve to illustrate the invention. In the accompanying drawings.

EXAMPLE 1

Growth of M. tuberculosis and Selection for a Phenotypically but not Genetically Rifampicin Resistant Population of Cells M. tuberculosis H37Rv was grown in Middlebrook 7H9 broth containing 0-05% Tween® 80 supplemented with 10% ADC, without agitation or other disturbance for up to 100 days, in accordance with the procedure of Wayne (1976) Amer. Rev. Resp. Dis. 114: 807-811. Where the stationary phase organisms were viable they were resistant to MIC levels of 0.1 μg/ml rifampicin.

Sixty 10 ml samples of the cultures were vortexed with glass beads for 3-5 minutes, followed by sonication in a water bath sonicator for less than 5 minutes. All the cultures were pooled into a 500 ml sterile bottle with screw cap.

Prior to addition of rifampicin, samples of the culture were taken to check purity, viability and metabolic activity as follows:

1. 2×100 μl for CFU counts
2. 2×5 ml for broth counts
3. 2×10 ml for [$^3$H]uridine counts,
4. 2×5 ml for [$^{35}$S]methionine counts
5. 10 ml for RNA extraction for RT-PCR
6. 10 ml for drug-free control
7. 20 μl for blood agar to check sterility Selection and Detection of a Rifampicin-Resistant Subpopulation 50 ml of 1000 μg/ml rifampicin was added to 500 ml of the above culture to obtain a final rifampicin concentration of 100 μg/ml, and the culture was incubated at 37° C. for 5 days. The cells were then harvested in sterile 50 ml tubes by centrifugation at 5000 g for 15 minutes, then washed twice in sterile PBS containing 0.05% Tween® 80 and Selectitab® antibiotics (which comprises a combination of antibacterial agents which kills most bacteria but not *M. tuberculosis*, thus preventing *M. tuberculosis* from becoming overgrown by faster growing bacteria). The cells were resuspended in 500 ml fresh 7H9 medium.

Sterility of the culture was checked before further experiments. 2×100 μl samples of the culture was added to blood agar plates in duplicate which were incubated at 37° C. overnight. The cell suspension was kept at 4° C. overnight. Contaminated cultures should always be discarded.

It was found that this treatment with high levels of rifampicin reduced plate counts to zero colony forming units but resulted in a small number of persisting organisms which were detectable by broth dilution counting. Table 1 shows a typical example of such selection where $10^2$ bacteria/ml remained from $10^6$ after one day of rifampicin treatment. From this, it appears that *M. tuberculosis* has at least two populations of stationary phase organisms: the first is killed by high dose rifampicin and the second 'persists' and is phenotypically resistant. Upon resumption of growth, the rifampicin-resistant stationary phase subpopulation becomes sensitive to rifampicin at the normal MIC level of 0.1 μg/ml.

EXAMPLE 2

Characterisation of the Rifampicin-Resistant Subpopulation In Vitro

Methods

*M. tuberculosis* was grown in 7H9 medium containing 0.05% of Tween® 80 supplemented with 10% ADS (Difco Laboratories) without shaking for 100 days. Rifampicin was added to the cultures at a final concentration of 100 μg/ml for 5 days. Viability was estimated at one day intervals. The cells were thoroughly washed and 100 μl of samples from 10-fold dilutions of the cultures were added to triplicate plates of Middlebrook 7H11 medium supplemented with OADC (Difco Laboratories). Colony forming units (CFU's) were counted after incubation of the plate for 3 weeks at 37° C. Broth counts were performed at 10-fold dilutions by adding 1 ml of the sample to 9 ml of 7H9 medium. Viability was estimated by examining growth in the diluted cultures after incubation for 6 weeks at 37° C.

For incorporation of radioactive uridine, 10 ml of the culture for each time point was washed twice to remove the remaining rifampicin and then resuspended in 10 ml 7H9 medium followed by incubation with 10 μCi/ml of [$^3$H]-uridine for 20 hours. For 5* the culture was not washed after incubation with rifampicin and 10 μCi/ml of [$^3$H]-uridine was added to the culture which was further incubated in the presence of rifampicin for 20 hours. The RNA was extracted by methods known in the art. The RNA [$^3$H]-uridine incorporation was determined as counts per minute of trichloroacetic acid precipitated RNA. The results were confirmed in three independent experiments.

The metabolic state of bacilli before and after rifampicin treatment was also assessed by examining total RNA which was extracted. RT-PCR was performed on the following genes; rpoB which encodes the rifampicin target (RNA polymerase sub-unit B); 16 kDa protein α-crystallin homolog); 16S rRNA and two Sigma 70 homologues, sigA and sigB.

Results

The results are shown in Table 1.

TABLE 1

Incorporation of [$^3$H]-uridine into *M. tuberculosis* after addition of rifampicin

| Days in rifampicin | Plate counts | Broth counts | [$^3$H]-uridine |
|---|---|---|---|
| 0 | $6.6 \times 10^5$ | $10^6$ | 74682 ± 630 |
| 1 | 0 | $10^2$ | 2228 ± 88 |
| 2 | 0 | $10^2$ | 2316 ± 120 |
| 3 | 0 | $10^2$ | 2430 ± 54 |
| 4 | 0 | $10^2$ | 2318 ± 126 |
| 5 | 0 | $10^2$ | 2388 ± 20 |
| 5* | 0 | $10^2$ | 518 ± 10 |
| 0 | 0 (heat-killed) | 0 | 180 ± 19 |

Samples of the rifampicin resistant subpopulation of cells were analysed and the cell population further characterised. The population was shown to be metabolically active by virtue of transcriptional and translational activity detected in the population. All the genes which were examined were found to be transcribed in the stationary phase. After 5 days of rifampicin treatment which reduced the cfu to zero, the 16S rRNA was not diminished and transcripts for rpoB, 16K and SigB could still be detected, albeit at reduced levels, whilst the transcript for SigA was not seen.

Broth dilution counts of rifampicin treated cultures (days 1-5) gave values of $10^2$ bacteria/ml (Table 1) indicating the presence of bacteria capable of growth. However, in spite of the four log drop in broth dilution counts after rifampicin treatment, the RT-PCR signal for 16S, sigB, 16K and rpoB was several log fold above that which would be expected for such low numbers of broth positive surviving bacteria. In order to quantitate the amount of 16S rRNA which was present, the rRNA level was measured by Northern blotting before and after treatment with rifampicin (data not shown). Densitometric analysis revealed that about half of the signal intensity remained after 7 days of treatment with the antibiotic in both log-phase and stationary phase organisms. This suggests that rRNA is very stable in rifampicin-treated cultures. In contrast, the mRNAs were much less stable than rRNA. The half-lives of mRNAs for 16K and sigB were measured in both log-phase and long term stationary phase cultures and were shown to be between 2-3 mins. Thus, it is unlikely that the RT-PCR results are accounted for by long term stable mRNA and suggest active transcription. This was tested by first treating organisms with rifampicin, and then incubating these bacteria simultaneously with rifampicin and [$^3$H]-uridine. In the presence of rifampicin the bacteria incorporated [$^3$H]-uridine indicative of active transcription in persisting bacteria, even in the presence of a high concentration of rifampicin and shows that the bacteria are actively metabolising.

The cells were shown to be very responsive to changes in their environment. When rifampicin was removed and replaced by growth medium alone, the level of transcription of three genes (16K, sigA and rpoB transcripts) analysed increased by 5- to 10-fold after 12 hours. Radioactive uridine incorporation also increased about 5-fold after removal of rifampicin and incubation with medium alone (Table 1—compare counts at 5* and 5 days). This suggested that the level of transcription increased rapidly under these circumstances. The data do not exclude the possibility that the organisms replicate in the presence of fresh medium, although this would only account for a two-fold rise in transcription in 12 hours, since the generation time of *M. tuberculosis* is about 20 hours. The data support a hypothesis that, in this in vitro model of drug resistant stationary-phase bacteria, there is a major population of bacteria that are actively transcribing RNA and are environmentally reactive, yet remain plate culture negative.

To distinguish between phenotypic and genotypic resistance the bacteria were thoroughly washed after rifampicin treatment and cultured in liquid 7H9 medium for 6 weeks. In four separate experiments *M. tuberculosis* was invariably grown. These bacteria were sensitive to 0.1 μg/ml rifampicin and were negative for rifampicin resistant mutations in rpoB as detected by RT-PCR and hybridisation with oligonucleotide probes (Immunogenetics N.V., Netherlands; data not shown). This indicates that the resistance is phenotypic in this model.

It is unlikely that the mechanism of induced resistance depends on mutation or reduced levels of expression of rpoB mRNA (i.e. resulting in a reduced level of drug target) because transcription continues even in the presence of rifampicin (Table 1).

Characterisation of the Antibacterial-Resistant Subpopulation In Vivo

Methods

The antibacterial-resistant subpopulation was examined in vivo according to the Cornell dormancy model in which murine chronic tuberculosis is induced by chemotherapy. *M. tuberculosis* was grown in BALB/c mice weighing 18-20 g which were infected intravenously with $2 \times 10^5$ cfu of a mouse-passaged, virulent H37Rv strain of *M. tuberculosis*. Spleens and lungs were removed rapidly after sacrifice and sterile autopsy at time point −2 week and 0 week (2 weeks after infection); portions of the organs were immediately frozen in liquid $N_2$.

Cfu counts of viable *M. tuberculosis* were done by grinding the spleen and lungs in 5 ml water in motor-driven polytetrafluoroethylene/glass grinders and setting up counts from serial dilution of the homogenate on plates of selective 7H11 medium (Difco, Detroit).

Treatment was then given for 14 weeks with 1000 mg pyrazinamide/kg and 25 mg isoniazid/kg body weight in the pelleted diet when the "sterile state" was reached. A sample of mice was also sacrificed at the 7 week timepoint. A further sample was then sacrificed at timepoint 14, and the entire organ homogenates were cultured in selective Kirchner liquid medium (Lab M, Amersham). Culture media were made selective for *M. tuberculosis* by the addition of 200 U polymyxin B/ml, 100 μg carbenicillin/ml, 20 μg trimethoprim/ml and 10 μg amphotericin/ml. During a further 8 weeks the remaining sample of mice were administered steroid therapy.

Results

RT-PCR of RNA from lungs removed before treatment revealed transcripts for rpoB, sigA, sigB, 16K and 16S rRNA. Significantly, bacterial mRNA for sigB and 16K was detected in lungs from day 91 (13 weeks) post treatment and the level of 16S rRNA was not reduced compared to the pre-chemotherapy level. It is surprising to find any mRNA at all after 13 weeks of chemotherapy since mRNA is depleted within a few hours. However, since we were not able to measure the half-life of mRNA in vivo or the uptake of [$^3$H]-uridine into RNA, we could not discriminate between unstable and stable mRNAs. Nevertheless, the data suggest that, substantial numbers of persisting bacilli are present in the lungs at day 91 which may be metabolically active because they contain mRNA, but are not culturable. All lungs used for RT-PCR were culture negative.

As in the in vitro model, the sigA transcripts were not detectable in mouse persisters and this may be due to low abundance of this mRNA leading to levels below detectable limits, or it could be due to insensitive primers. Current data do not discriminate between these possibilities. The sigF transcripts (data not shown) were detected in the Cornell mice but the bands were very weak. All controls were performed to ensure RT-PCR products derived from mRNA and not from contaminating genomic DNA.

Two weeks after infection, at time 0 week, a sample of 4 mice yielded $2-5\times10^7$ cfu/lungs or spleen. Four further mice were sacrificed at 7 and 14 weeks. Of these 8 mice two yielded a positive organ culture, one from the spleen only and one from the lungs. However, mice in this "sterile" state contain large amounts of M. tuberculosis DNA which is estimated to be equivalent to $10^5$ bacteria per organ. Upon treatment of the mice with steroids, spleens and lungs yielded positive cultures indicating reactivation from a dormant, non-culturable and drug insensitive state.

Without wishing to be bound by theory it is believed that the mechanism of resistance of the persistent bacteria to antibacterial agents may be due to a decrease in cell wall permeability (EDTA permeabilizes persister cell walls and increases the efficacy of rifampicin, data not shown) and the use of alternative sigma factors (such as sigB) which confer insensitivity to the rifampicin-mediated inhibition of transcription.

Susceptibility Assessment of Drug Libraries

Sterile 0.7 ml labelled transparent plastic snap-capped tubes containing 1-20 µg of the compound to be tested are used. The compound is dissolved in 0.25 ml of sterile distilled water or other appropriate diluent. 0.25 ml of the rifampicin treated culture is added to each tube in the class I cabinet in a category III safety containment laboratory with care being taken to avoid contamination. The tubes are incubated at 37° C. The drug effects are examined by CFU counts by addition of 2×50 µl of each sample to 7H11 agar plates in duplicate including 2 drug-free controls at 1 week intervals. A series of 10-fold dilutions of the samples may be required, which is made in 7H9 broth with 0.05% Tween 80 but without ADC, then the diluted samples are plated on 7H11 agars and the concentration effect of the candidate compounds determined.

EXAMPLE 3

Selection of Phenotypically but not Genotypically Resistant Subpopulations of E. coli and S. aureus Using Kanamycin and Ampicillin Respectively Growth of Escherichia coli and Staphylococcus aureus Escherichia coli K12 and Staphylococcus aureus are grown in 10 ml of nutrient broth No. 2 (Oxoid) with continuous shaking at 120 rpm for 10 days. Viability of the bacteria is estimated by colony forming unit counts at 2 hours intervals for the first 24 hours and 12-24 hours afterward. From serial 10-fold dilutions of the experimental cultures, 100 µl samples are added to triplicate plates of nutrient agar plates (Oxoid). Colony forming units (CFU) are counted after incubation of the plates at 37° C. for 24 hours.

Selection of Persistent Bacteria by Antibiotics

Figure 1:
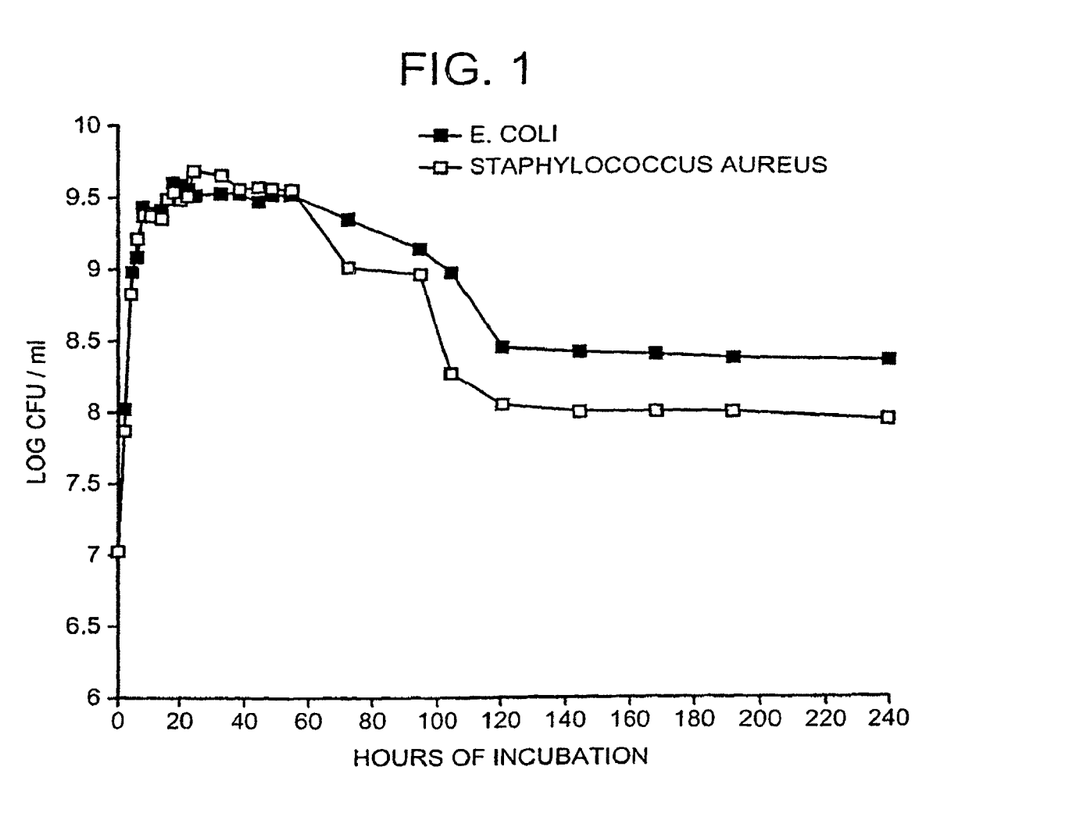
FIG. 1 shows growth curves for E. coli and S. aureus over a period of 10 days.
Figure 2:
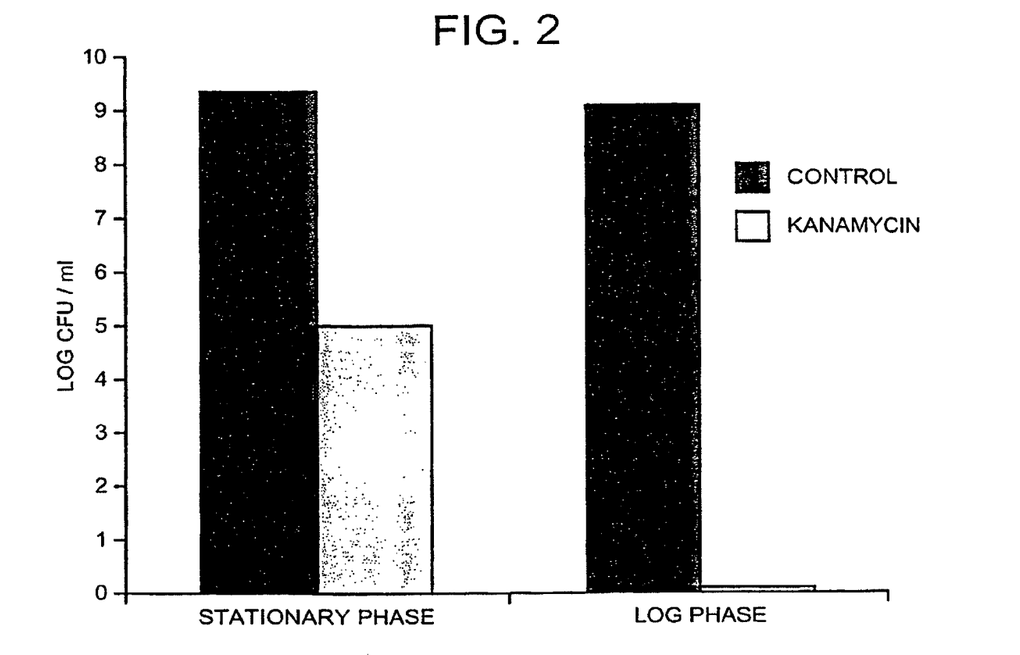
FIG. 2 shows the viability of E. coli after treatment with 50 µg/ml kanamycin during stationary phase and log phase growth.
Figure 3:
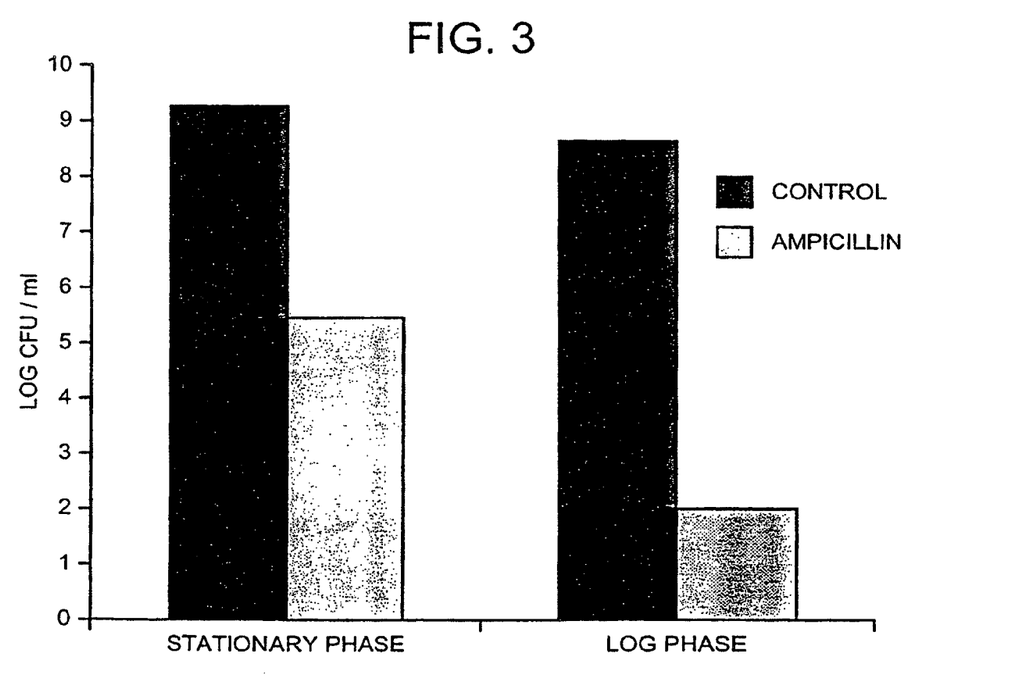
FIG. 3 shows the viability of S. aureus after treatment with 100 µg/ml ampicillin during stationary phase and log phase growth.

Ampicillin and kanamycin are added to 5-day stationary-phase cultures of S. aureus and E. coli, respectively, to a final concentration of 100 µg/ml and 50 µg/ml, respectively, for 3 days. After 3 days of antibiotic treatment, the cells are washed with sterile distilled water 3 times, then resuspended in 10 ml fresh nutrient broth. Viability is estimated by CFU counts and broth dilution counts. Broth dilution counts are performed in a serial 10-fold dilution in nutrient broth, then 1 ml of each dilution in added into 9 ml of nutrient broth in 30-ml universal tubes in triplicate. The growth curves for E. coli and S. aureus over the 240 hour period in the absence of antibiotics is shown in FIG. 1. The effect of antibiotic exposure on the E. coli and S. aureus during both log and stationary phase of growth is shown in FIGS. 2 and 3. Treatment of the cultures during stationary phase results in the selection of an antibiotic resistant subpopulation of cells.

The invention claimed is:

1. A method for assessing an antibiotic activity of a test compound against metabolically active, non-growing bacteria, for screening for identification of new antibacterial agents, the method comprising steps of:
    (a) contacting a stationary phase bacterial culture with an antibiotic agent to select a sub-population of metabolically-active, non-growing live bacteria, wherein said sub-population is insensitive to the antibiotic agent while metabolically-active and non-growing, but sensitive to said antibiotic agent if induced to an active growth state; and
    (b) contacting a sample of metabolically-active, non-growing bacteria from said sub-population with a test compound that is different from the antibiotic agent and determining a number of live bacteria following the contacting, wherein a reduction in the number of live bacteria after contacting said sample with said test compound, compared to a number of live bacteria in a control sample untreated with the test compound, is indicative of said test compound having antibacterial activity against metabolically active, non-growing bacteria.

2. The method as claimed in claim 1, wherein the antibiotic agent is selected from the group consisting of rifampicin, kanamycin, ampicillin and pyrazinamide.

3. The method as claimed in claim 1, wherein step (a) comprises contacting the bacterial culture with the antibiotic agent at a concentration of at least ten times the minimum inhibitory concentration (MIC) of the antibiotic agent, such that all actively growing bacteria are killed, so as to obtain a subpopulation of metabolically active non-growing live bacteria.

4. The method as claimed in claim 1, wherein in step (a) the stationary phase bacterial culture contains $10^5$ to $10^9$ bacteria/ml prior to contacting with the antibiotic agent.

5. The method as claimed in claim 1, wherein the bacteria are a strain of a species selected from the group consisting of the Staphylococcus aureus, Escherichia coli, Haemophilus influenzae, Streptococcus pyogenes, Streptococcus gordonii and Mycobacterium tuberculosis.

6. The method as claimed in claim 1, wherein the bacteria are a strain of Mycobacterium tuberculosis and said antibiotic agent is rifampicin.

7. The method as claimed in claim 1, wherein the bacteria are a strain of Escherichia coli and said antibiotic agent is kanamycin.

8. The method as claimed in claim 1, wherein the bacteria are a strain of Staphylococcus aureus and said antibiotic agent is ampicillin.

9. The method as claimed in claim 1, further comprising a step, prior to the contacting step (a), of growing a population of the bacteria in culture media in the absence of the antibiotic agent until the bacteria reach stationary phase.

10. The method as claimed in claim 1, further comprising verifying that the subpopulation of bacteria selected according to step (a) contains metabolically active, non-growing live bacteria that are sensitive to said antibiotic agent if induced to an active growth state by:
   contacting a sample of the selected subpopulation with culture media in the absence of the antibiotic agent to induce live bacteria present in the subpopulation to resume active growth and to obtain a growing bacteria sample; and
   contacting the growing bacteria sample with culture media containing said antibiotic agent at its MIC or up to $10^4$ times its MIC, and determining whether actively growing bacteria present in said growing bacteria sample are killed by said antibiotic agent, wherein the killing of actively growing bacteria present in said growing bacteria sample by the antibiotic bacterial agent verifies that the subpopulation selected in step (a) are sensitive to said antibiotic agent if induced to an active growth state.

11. The method as claimed in claim 1, comprising performing step (b) to screen a library of compounds for antibiotic activity against metabolically active, non-growing bacteria.

12. A method for assessing an antibiotic activity of a test compound against metabolically active, non-growing bacteria, for screening for identification of new antibacterial agents, the method comprising steps of:
   (a) contacting a stationary phase bacterial culture with an antibiotic agent to select a sub-population of metabolically-active, non-growing live bacteria, wherein said sub-population is insensitive to the antibiotic agent while metabolically-active and non-growing, but sensitive to said antibiotic agent if induced to an active growth state;
   (b) contacting metabolically-active, non-growing live bacteria from the sub-population with a test compound that is different from the antibiotic agent; and
   (c) assessing antibacterial activity of the test compound against metabolically active, non-growing live bacteria by measuring metabolic activity of the bacteria after the contacting, wherein reduced metabolic activity after the contacting, compared to metabolic activity in the absence of contact with the test compound, is indicative of the test compound having antibacterial activity against said metabolically-active, non-growing live bacteria.

13. The method as claimed in claim 12, comprising performing steps (b) and (c) to screen a library of compounds for antibiotic activity against metabolically active, non-growing bacteria.

14. A method for assessing an antibiotic activity of a test compound against metabolically active, non-growing bacteria, for screening for identification of new antibacterial agents, the method comprising steps of:
   (a) contacting a stationary phase bacterial culture with an antibiotic agent to select a sub-population of metabolically-active, non-growing live bacteria, wherein said sub-population is insensitive to the antibiotic agent while metabolically-active and non-growing, but sensitive to said antibiotic agent if induced to an active growth state;
   (b) contacting metabolically-active, non-growing live bacteria from the sub-population with a test compound that is different from the antibiotic agent; and
   (c) assessing antibacterial activity of the test compound by assessing the ability of the metabolically-active, non-growing live bacteria to form colonies after resuscitation in liquid culture, wherein a reduction in number of colony forming units after resuscitation following the contacting with the test compound, relative to a number of colony forming units following resuscitation in liquid culture in the absence of contact with the test compound, is indicative of the test compound having antibacterial activity against said metabolically-active, non-growing live bacteria.

15. The method as claimed in claim 14, comprising, performing steps (b) and (c) to screen a library of compounds for antibiotic activity against metabolically active, non-growing bacteria.

* * * * *